(12) United States Patent
Gustin

(10) Patent No.: US 8,057,741 B2
(45) Date of Patent: Nov. 15, 2011

(54) GAS SENSOR ASSEMBLY

(75) Inventor: Ronald R. Gustin, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 176 days.

(21) Appl. No.: 12/341,069

(22) Filed: Dec. 22, 2008

(65) Prior Publication Data

US 2010/0158758 A1 Jun. 24, 2010

(51) Int. Cl.
*G01N 31/12* (2006.01)
(52) U.S. Cl. .......................................... 422/94
(58) Field of Classification Search .................. 422/94
See application file for complete search history.

(56) References Cited

U.S. PATENT DOCUMENTS

| | | |
|---|---|---|
| 3,819,500 A | 6/1974 | Van Esdonk et al. |
| 3,940,327 A | 2/1976 | Wagner et al. |
| 4,105,524 A | 8/1978 | Fujishiro et al. |
| 4,132,615 A | 1/1979 | Linder et al. |
| 4,157,282 A | 6/1979 | Riddel |
| 4,157,948 A | 6/1979 | Maurer |
| 4,200,511 A | 4/1980 | Sato et al. |
| 4,212,720 A * | 7/1980 | Maurer et al. ............. 204/424 |
| 4,339,318 A | 7/1982 | Tanaka et al. |
| 4,383,906 A | 5/1983 | Sano et al. |
| 4,588,493 A | 5/1986 | Blumenthal et al. |
| 4,908,119 A | 3/1990 | Saito et al. |
| 4,980,042 A | 12/1990 | Shiomi et al. |
| 5,271,816 A | 12/1993 | Tanaka et al. |
| 6,235,174 B1 | 5/2001 | Jaurnig |
| 2004/0149595 A1* | 8/2004 | Moore ................. 205/784.5 |
| 2006/0042946 A1 | 3/2006 | Tsukahara et al. |

\* cited by examiner

*Primary Examiner* — Bobby Ramdhanie
(74) *Attorney, Agent, or Firm* — Finnegan, Henderson, Farabow, Garrett & Dunner LLP

(57) ABSTRACT

A gas sensor assembly may include a housing defining a chamber. A gas sensor may be mounted in the chamber. An inlet tube may be secured to the housing and extend into the chamber of the housing. The inlet tube may define a passage providing fluid communication between outside the housing and the chamber of the housing.

14 Claims, 10 Drawing Sheets

FIG. 5
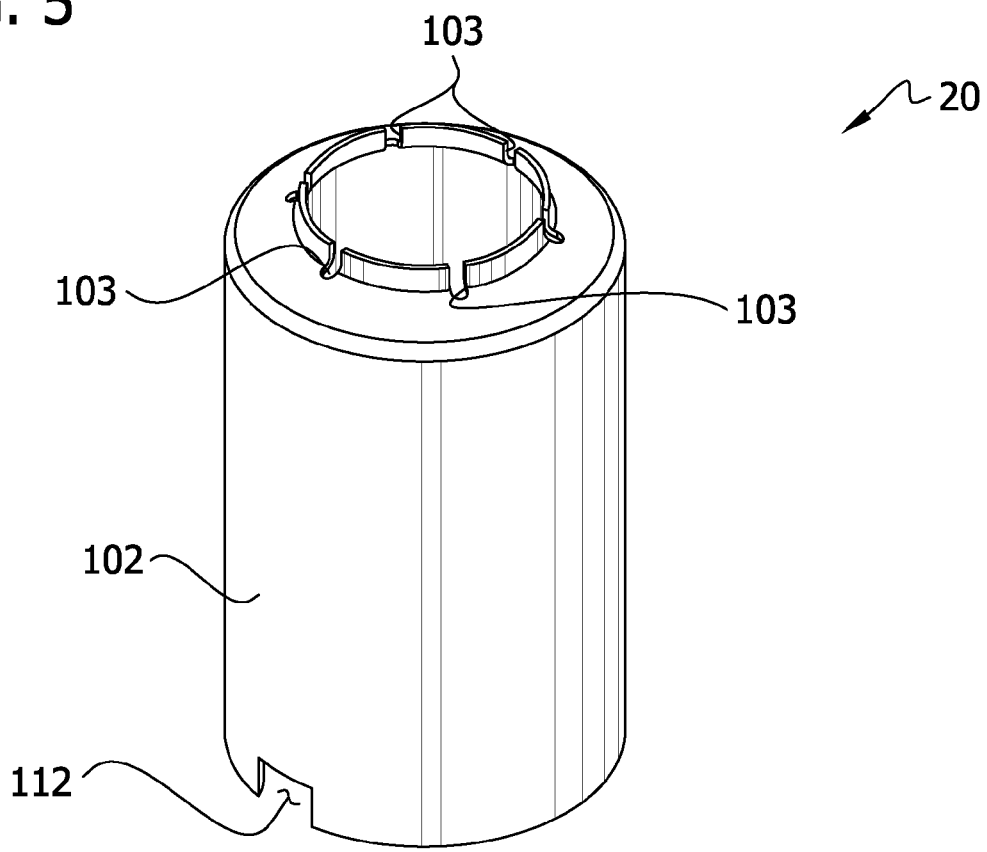
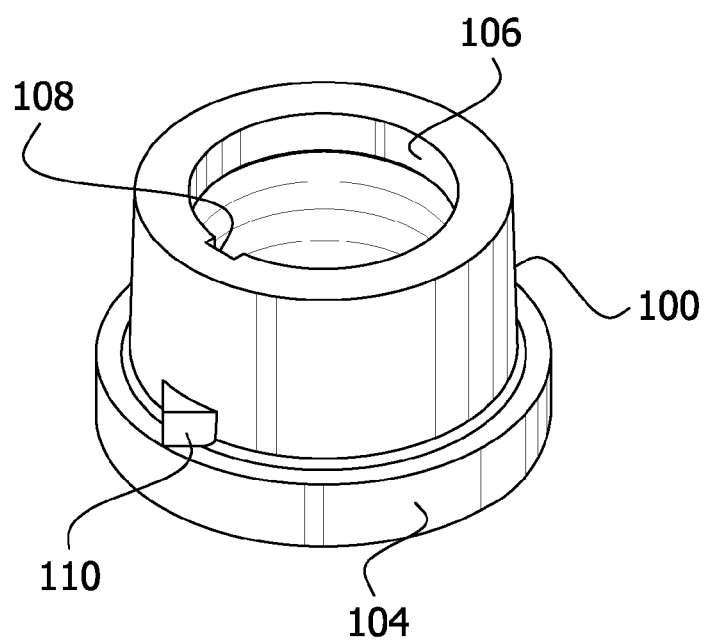

GAS SENSOR ASSEMBLY

TECHNICAL FIELD

This invention relates general to a gas sensor assembly.

BACKGROUND

Combustion of hydrocarbon fuel, such as in an internal combustion engine, produces exhaust gas composed of a mixture of constituent gases, including oxide gases (e.g., $NO_X$, $SO_X$, $CO_2$ and CO), unburned hydrocarbons and $O_2$. It is advantageous to accurately measure the concentration of one or more of these constituent gases in the exhaust gas in real time. For example, accurate, real time concentration measurements of $NO_X$ gas can be used as part of a feedback loop for ensuring that the emissions of $NO_X$ gas from an internal combustion engine are maintained at an acceptable amount.

U.S. Pat. No. 7,217,355 issued to Nair et al. on May 15, 2007, discloses a gas sensor for detecting concentration of $NO_X$ gas in a stream of gas. The sensor includes a cylindrical housing with an open end constituting an inlet through which a stream of gas enters the sensor. An input assembly including a catalyst assembly is secured in the housing adjacent to the inlet. A heating rod is used to heat the sensor to an optimal operating temperature above the temperature of the gas stream. A $NO_X$ sensor electrode is received in the housing downstream from the input assembly. A gas exit port projects laterally from the housing near the $NO_X$ sensor electrode. The gas exit port comprises a small diameter stainless steel tube that, when connected to some type of suction device, will draw the exhaust gas stream through the input assembly and out the housing through the exit port. The suction device can be a small air pump, or the gas suction can be accomplished using the vacuum lines commonly implemented in internal combustion engines.

Requiring a pump or prime mover to pump gas through the sensor makes the sensor more difficult to install in a machine, particularly an exhaust system of a machine, and makes operation of the sensor dependent on other components of the machine, which can make troubleshooting more difficult. Moreover, where the housing is inserted in an exhaust tube and designed to sample the exhaust stream passing over the housing, the relatively cool exhaust gas will cool the components in the housing, requiring more power to drive the healing rod to maintain the sensors at the optimal operating temperature.

SUMMARY OF THE INVENTION

In one aspect of the present invention, a gas sensor assembly is provided. The gas sensor assembly may include a housing defining a chamber. A gas sensor element may be mounted in the chamber. An inlet tube may be secured to the housing and extend into the chamber of the housing. The inlet tube may have a passage providing fluid communication between outside the housing and the chamber of the housing.

In another aspect, a method of making a gas sensor assembly may comprise securing a gas sensor element in a chamber of a housing. An inlet tube may be secured to the housing in an arrangement so the inlet tube extends into the chamber of the housing and a passage of the inlet tube provides fluid communication between outside the housing and the chamber of the housing.

In yet another aspect, a gas sensor assembly may comprise a housing defining a chamber and having a length extending between opposite longitudinal ends. A gas sensor element in the chamber extends longitudinally with respect to the housing. An inlet tube is secured to the housing and extends into the chamber of the housing. The inlet tube has a passage extending longitudinally with respect to the housing and is arranged to provide fluid communication between outside the housing and the chamber of the housing. An outlet tube is secured to the housing and extends into the chamber of the housing. The outlet tube has a passage extending longitudinally with respect to the housing and is arranged to provide fluid communication between outside the housing and the chamber of the housing. The gas sensor element is positioned between the inlet tube and the outlet tube inside the chamber.

BRIEF DESCRIPTION OF THE DRAWINGS

FIG. 5 is a separated perspective of a housing mount of the gas sensor assembly;

DETAILED DESCRIPTION

Figure 1:
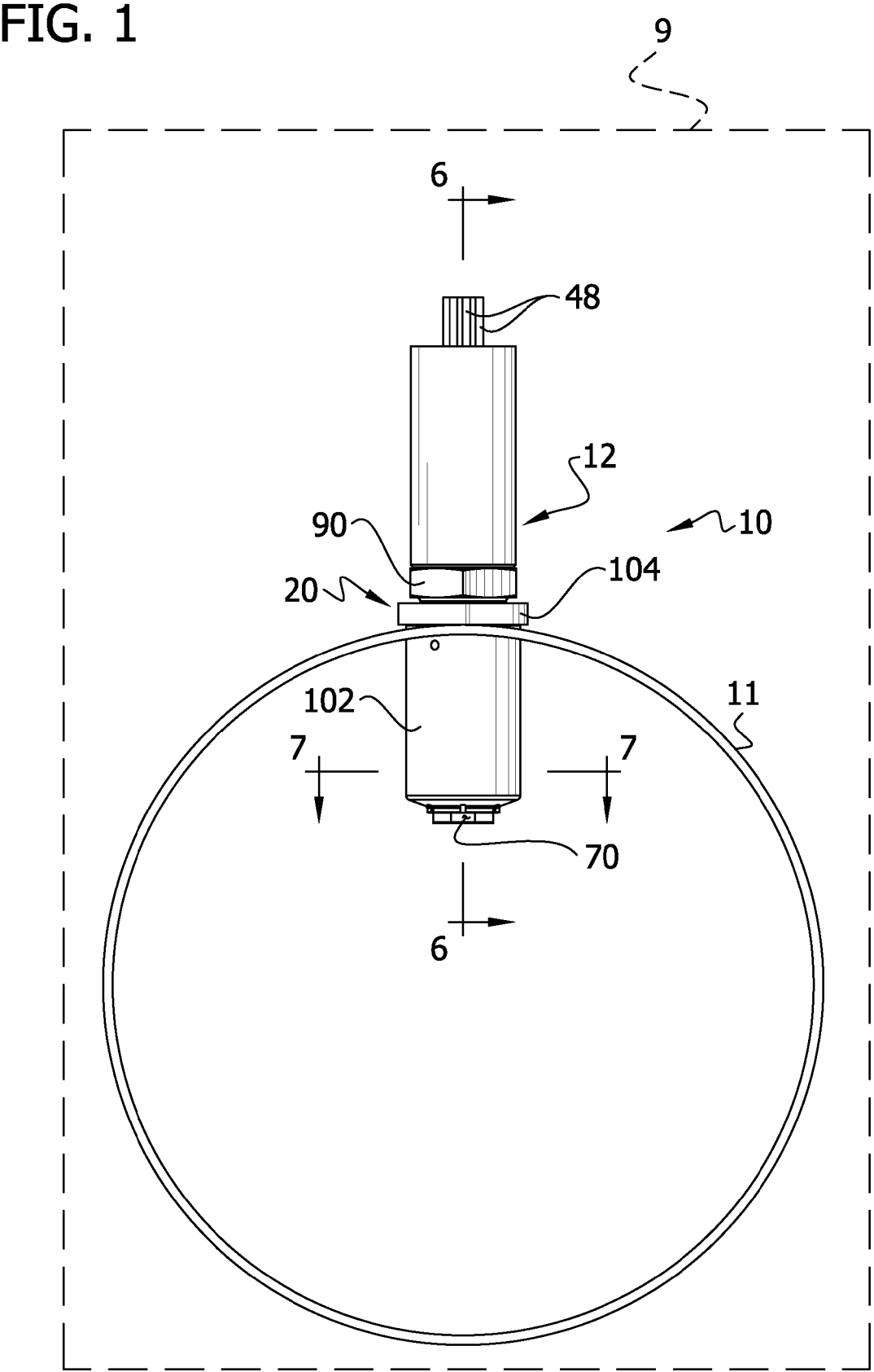
FIG. 1 is an elevation of a gas sensor assembly mounted on an exhaust tube of a machine.
Figure 2:
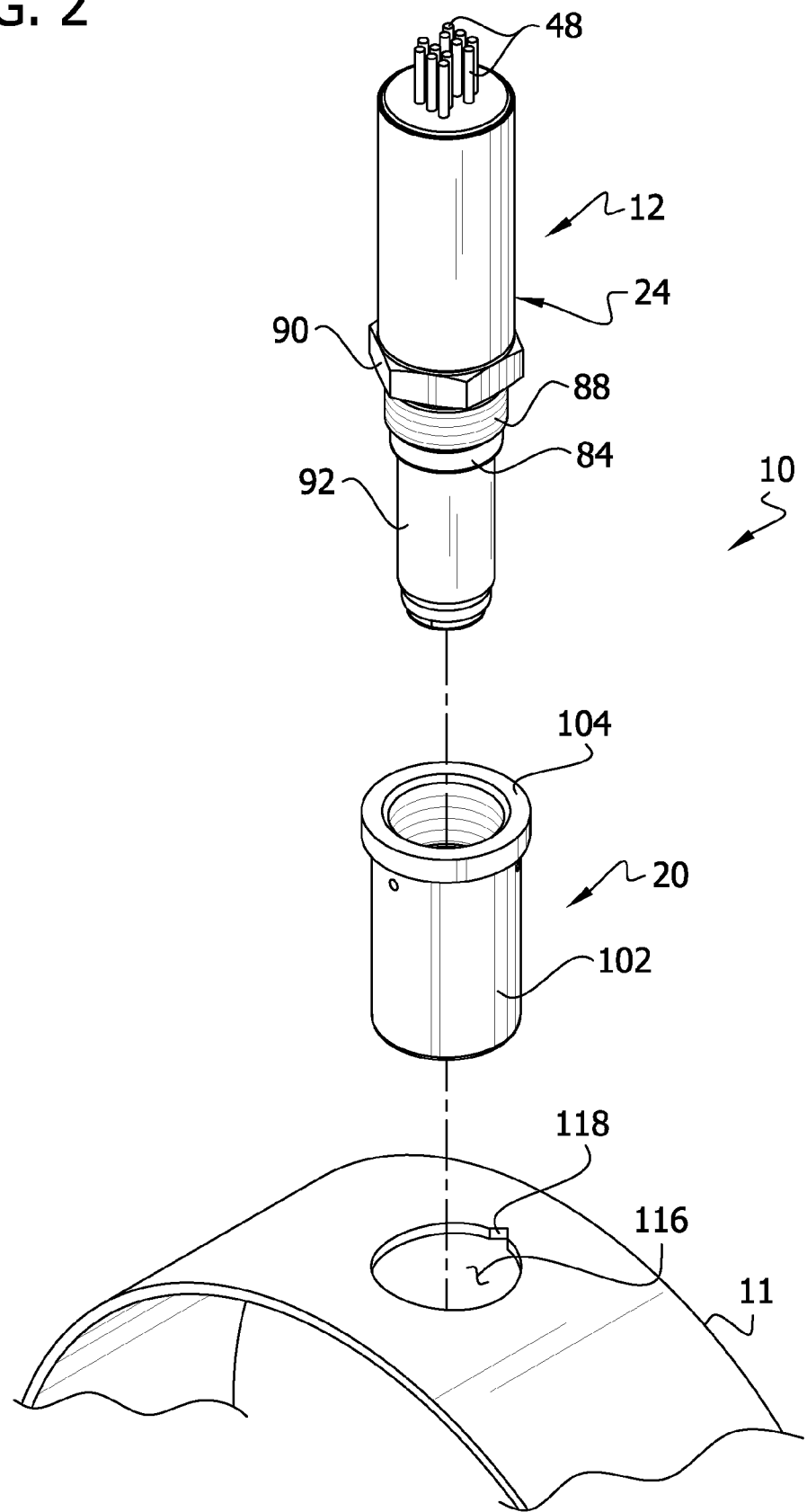
FIG. 2 is a separated perspective of the gas sensor assembly of FIG. 1 removed from the exhaust tube.
Figure 3:
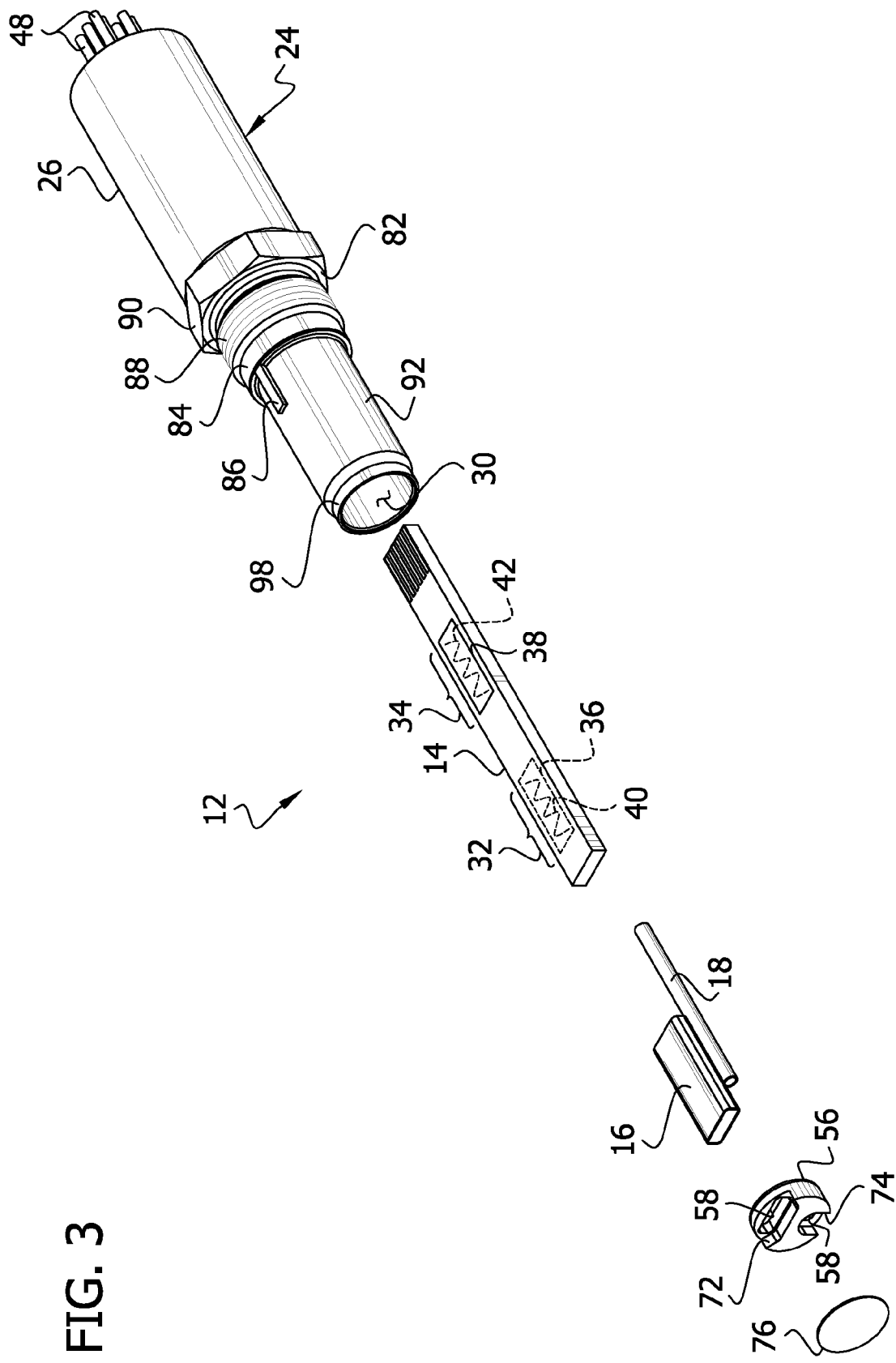
FIG. 3 is a separated perspective of a housing assembly of the gas sensor assembler showing internal components of the assembly.
Figure 6:
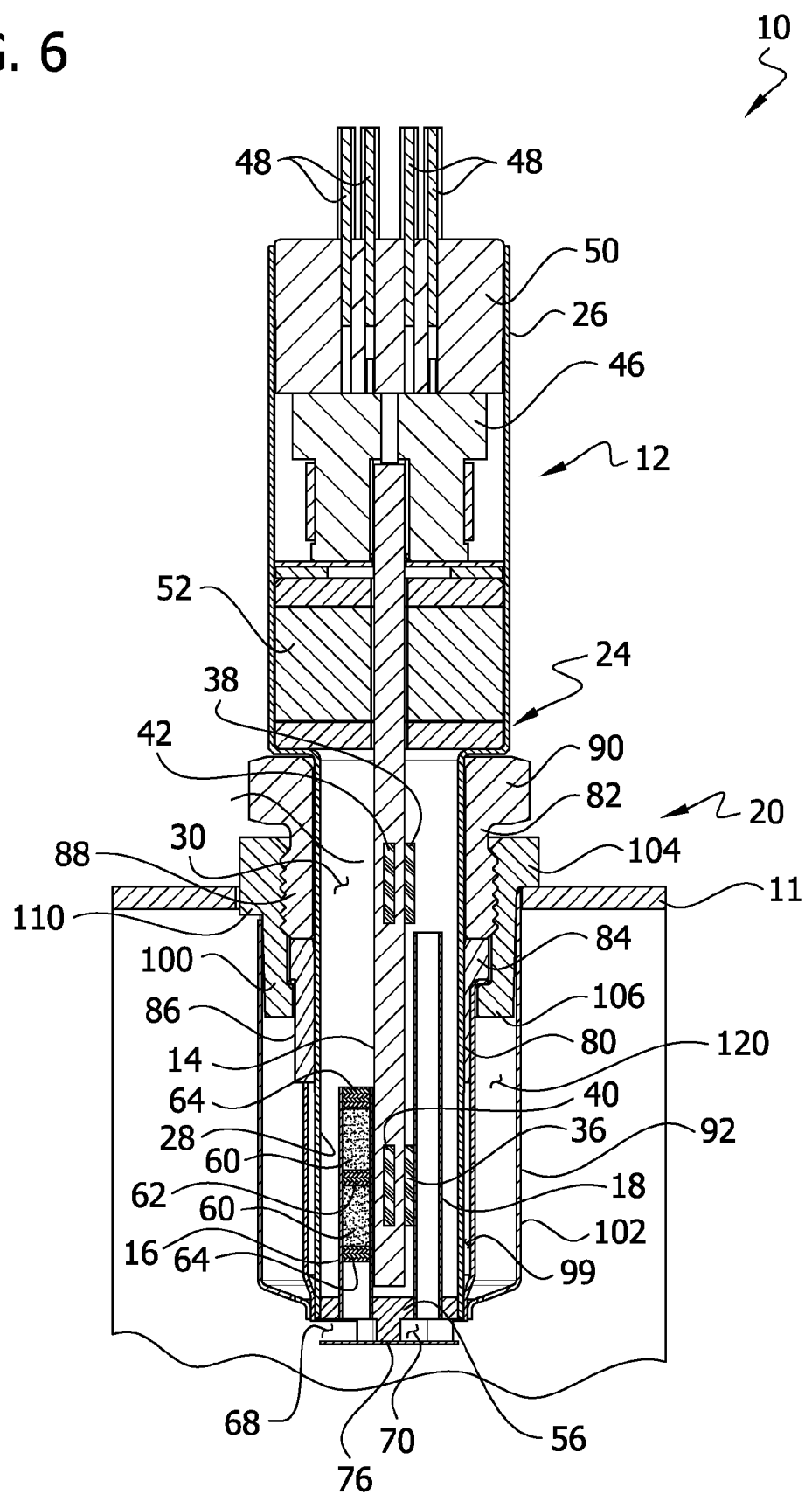
FIG. 6 is a section of the gas sensor assembled and exhaust tube of FIG. 1 taken along line 6-6 of FIG. 1.

Referring to FIGS. 1 and 2, a machine 9 includes one embodiment of a gas sensor assembly, generally indicated in its entirety by reference numeral 10, secured to a gas conduit or tube 11 through which a stream of gas, such as exhaust gas from an engine of the machine 9, flows. The gas sensor assembly 10 of the illustrated embodiment is constructed to take a sample of gas from the stream of gas and to generate one or more signals indicating one or more characteristics (e.g., concentration) of one or more constituent gases in the stream. Referring to FIGS. 3 and 6, in general the gas sensor assembly 10 includes a housing assembly 12 (broadly, a housing) enclosing a gas sensor element 14, and inlet and outlet tubes 16, 18, respectively, extending into the housing assemble for respectively providing an entrance and an exit for the sampled gas taken from the gas stream. The gas assembly 10 also includes a housing assembly mount (broadly, a housing mount), generally indicated at 20, to mount the gas sensor assembly on the gas tube 11 in fluid communication with the gas stream.

Figure 4:
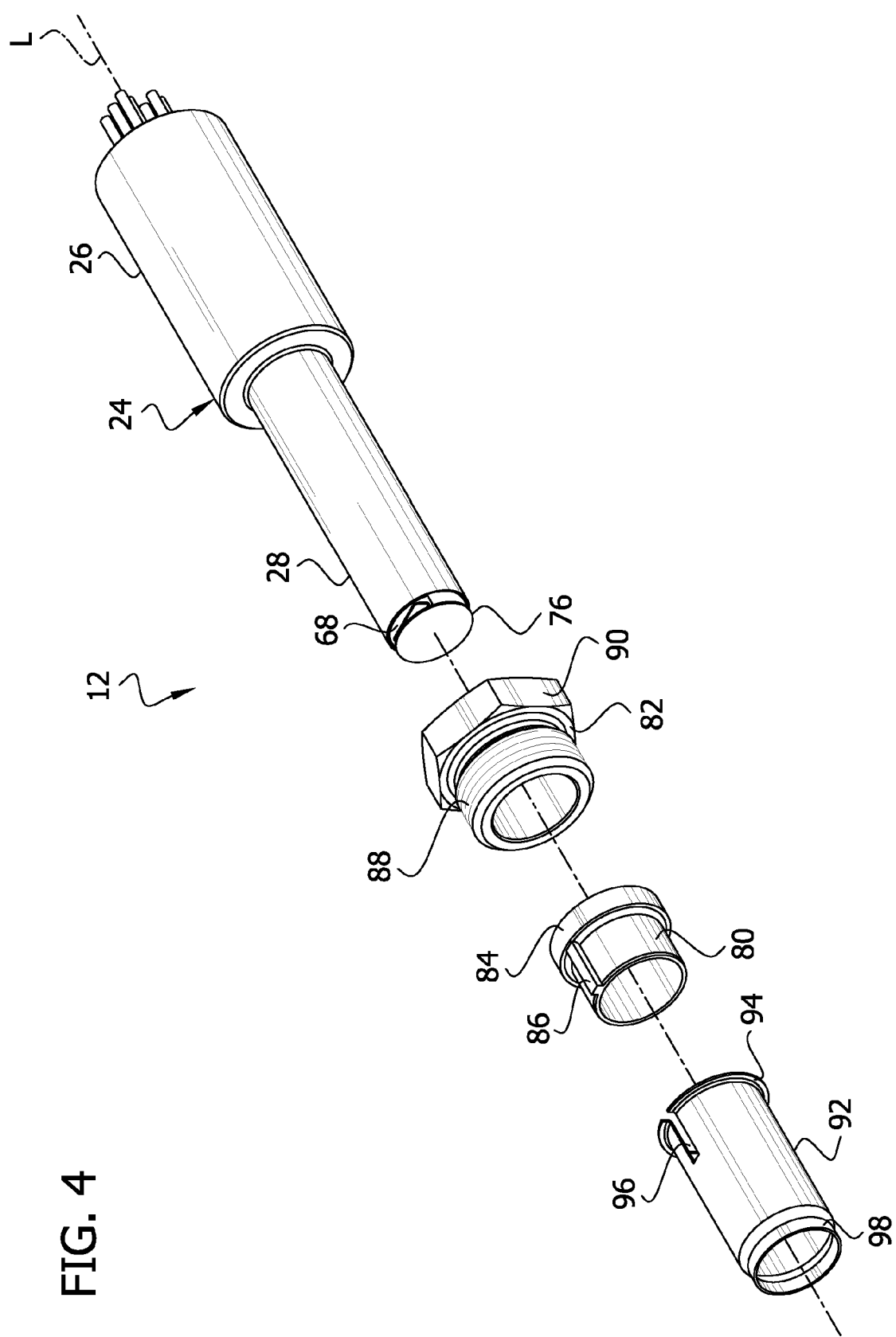
FIG. 4 is a separated perspective of the housing assembly of the gas sensor assembly showing external components of the assembly.

Referring to FIGS. 3, 4 and 6, the housing assembly 12 includes a generally cylindrical shell 24 having an open first longitudinal end portion 26, an open second longitudinal end portion 28 having a smaller diameter than the first end, and a longitudinal axis L extending between the first and second longitudinal ends. In one example, the shell 24 of the housing assembly 12 may be formed by deep drawing stainless steel, although other ways of making the shell do not depart from the scope of the present invention. The shell 24 may have other shapes and may be made in other ways within the scope of the invention.

The gas sensor element 14 is mounted within the first longitudinal end portion 26 of the shell 24 and extends along the length of the shell into a sampling chamber 30 defined by the second longitudinal end portion 28 of the shell. In the illustrated embodiment and as shown in FIG. 3, the gas sensor element 14 has a first detecting segment 32 to detect a concentration of a first constituent gas (e.g., oxygen), and a second detecting segment 34, spaced longitudinally from the first segment, to detect a concentration of a different second constituent gas (e.g. NOx gas). Each of the first and second detecting segments 32, 34 comprises a sensing component 36, 38, respectively, (e.g., a reference electrode and a sensing electrode), illustrated schematically in FIGS. 3 and 6, for detecting the respective constituent gas. Each of the detecting segments 32, 34 further includes a heater 40, 42, respectively, such as a resistance heating element illustrated schematically in FIGS. 3 and 6, for heating the corresponding sensing component to an optimal operating temperature, and a temperature sensor (not shown) for detecting the temperature at the detecting segment. For example, one type of NOx sensor has an optimal operating temperature in a range from about 300° C. to about 600° C., and more particularly, in a range from about 450° C. to about 550° C. One type of $O_2$ sensor has an optimal operating temperature of in a range from about 500° C. to about 900° C. and more particularly, in a range from about 700° C. to about 800° C. Ate sensing components 36, 38, the heaters 40, 42 and the temperature sensors may be formed as stacked layers that are separated by layers of ceramic material. Other types of sensor elements, other operating temperature ranges, and other ways of forming the sensor element may be used without departing from the scope of the invention.

Referring to FIG. 6, the gas sensor element 14 is inserted in a connector 46 in the first longitudinal end portion 26 of the shell 24 to electrically connect the sensing components 36, 38, the heaters 40, 42 and the temperature sensors to electrical wires 48 that extend out from the second longitudinal end 28 of the housing assembly 12 and connect electrically to a controller (not shown) and a power source (not shown). The electrical wires 48 extend through a bushing 50 secured in the first longitudinal end portion 26 or the shell 24, and the sensor element 14 extends through a seal 52 in the first longitudinal end portion of the shell adjacent to the second longitudinal end portion 28. The bushing 50 may comprise an elastic material and the seal 52 may comprise a compacted ceramic powder to prevent any moisture present in the second longitudinal end portion 28 of the shell 24 from entering the first longitudinal end portion 26. One or more electrical signals produced by the sensing components 36, 38 indicating the concentration of one or more constituent gases present in the sampling chamber 30 is communicated to the controller via one or more of the electrical wires 48. One or more electrical signals produced by the temperature sensors indicate the temperatures at the respective first and second detecting segments 32, 24. Power is supplied through one or more of the electrical wires 48 to operate the heaters 40, 42.

Referring to FIGS. 3 and 6, a mounting component 56 of the housing assembly 12 is secured to the open first longitudinal end of the shell 24. The inlet and outlet tubes 16, 18 are mounted on or secured to the mounting component 56 so that the inlet and outlet tubes extend into the sampling chamber 30 longitudinally with respect to the housing assembly 12. In general, gas flows into the sampling chamber 30 through the inlet tube 16 contacts the first and second sensing components 36, 38 on the sensor element 14, and then flows out the sampling chamber through the outlet tube 18. In the illustrated embodiment, the mounting component 56 is constructed as a circular plate or disk having a first or outer face facing away from the sampling chamber 30 and second or inner face facing the sampling chamber. The mounting component 56 may be formed from stainless steel or other material within the scope of the invention. The inlet and outlet tubes 16, 18 are received in and secured to the mounting component 56 within respective diametrically opposing mounting openings 58 extending through the outer and inner faces of the mounting component. In one example, the inlet and outlet tubes 16, 18 are welded to the mounting component 56, such as by laser welding, and the mounting component is inserted in and welded to the shell 24, such as by laser welding. Other ways of securing the inlet and outlet tubes 16, 18 to the mounting component 56 and other ways of securing the mounting component to the shell 24 may be used without departing from the scope of the present invention.

The inlet and outlet tubes 16, 18 may be formed by deep drawing stainless steel. The tubes 16, 18 may be formed in other ways, and may be made from other types or material without departing from the scope of the present invention. In the illustrated embodiment, a gas conditioner is contained in the inlet tube 16 to condition the exhaust gels before it enters the sampling chamber 30. It should be understood that the conditioner may be omitted from the inlet tube 16 without departing from the scope of the invention. The conditioner may include one or more different types of materials stacked as layers along the length of the inlet tube. For example, in the illustrated embodiment (FIG. 6) the conditioner comprises two conditioning layers 60 separated by a porous separator 62 and retained in the tube by porous retainers 64 adjacent to opposite longitudinal ends of the inlet tube. In the illustrated embodiment, a portion of the inlet tube 16 adjacent to the mounting component 56 is empty to prevent heat loss. The porous separator 62 and porous retainers 64 may comprise mesh screens, porous ceramic, porous powdered metal (e.g., stainless steel) or other materials and constructions that allow gas to flow through the material while respectively separating the conditioning layers 60 and retaining the layers in the inlet tube 16. The porous separator 62 may also include a layer of felt (not shown).

In the illustrated embodiment, one of the conditioning layers may comprise an oxidation catalyst (e.g., platinum loaded γ-alumina pellets) that converts NO to $NO_2$, and the other of the conditioning layers may comprise an ammonia ($NH_3$) catalyst that decomposes $NH_3$. It should be understood that in other examples, there may be one conditioning layer or more than two conditioning layers. Moreover, the conditioning layers may comprise other types of conditioners, including but not limited to an oxidation catalyst that oxidizes particulate matter (e.g., $CH_4$, CO), and an absorber (e.g., CaO) that absorbs a constituent in the exhaust gas.

Figure 7:
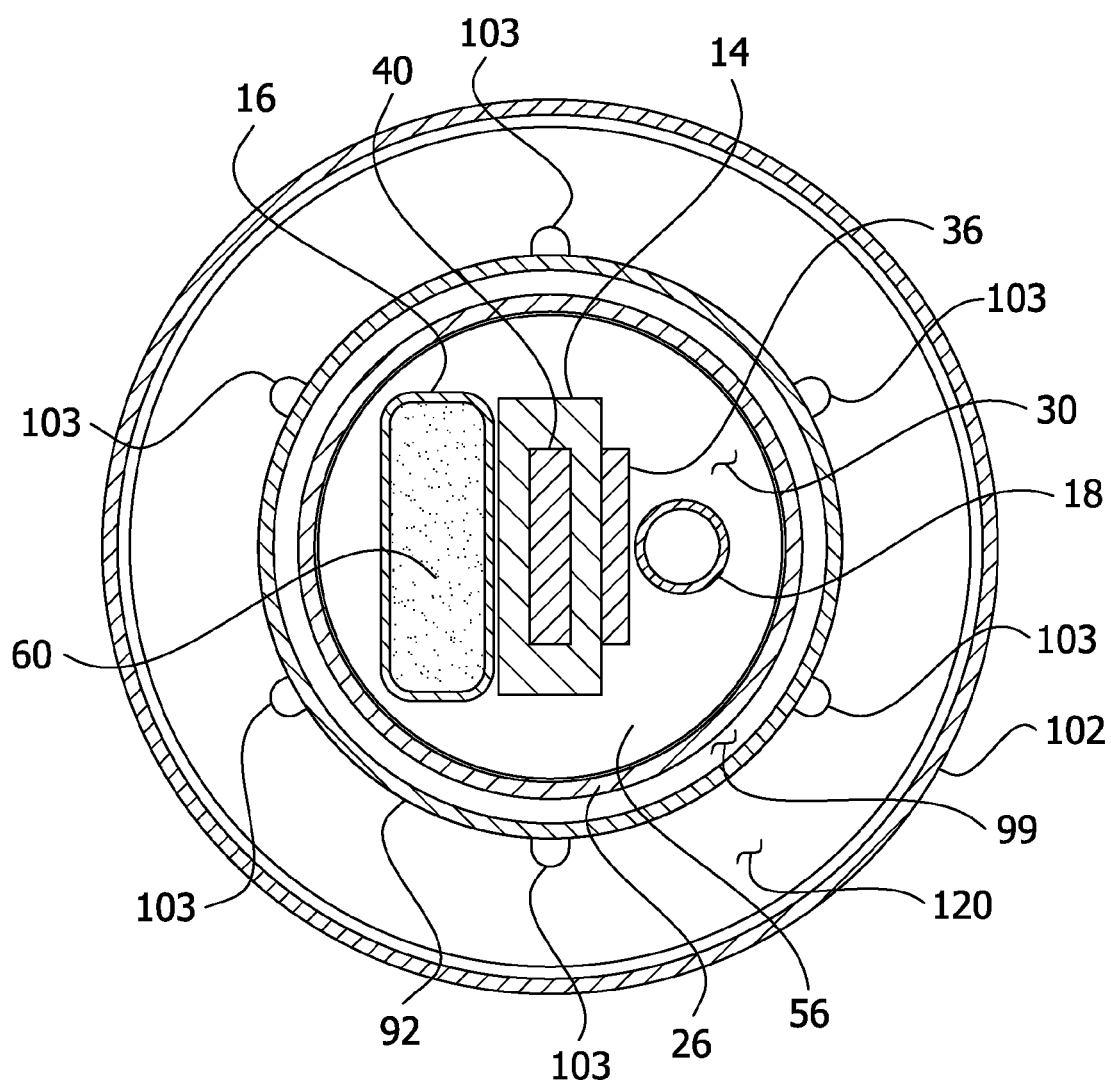
FIG. 7 is a cross section of the gas sensor assembly taken along line 7-7 of FIG. 1.

Referring to FIGS. 3, 6 and 7, the inlet and outlet tubes 16, 18 are situated on opposite sides or faces of the sensor element 14. In other words, the sensor element 14 is disposed between the inlet and outlet tubes 16, 18 in the sampling chamber 30. In the illustrated embodiment, at least a longitudinal portion of the inlet tube 16 and at least a longitudinal portion of the first detecting segment 32 are situated in a common plane extending generally transverse to the longitudinal axis of the shell 24. As will be explained below, the inlet tube 16 is situated upstream from the outlet tube 18 so the sampled gas taken from the gas stream flows across and around the sensor element 14 to the outlet tube. In the illustrated embodiment, the outlet tube 18 is longer than the inlet tube 16 and extends to a longitudinal position in the shell 24 that is closer to the second sensing component 38 than the inlet tube. This configuration ensures that the sampled gas will flow toward the second detecting segment 34 (e.g., the NOx detecting segment) before the gas enters the outlet tube 18 and exits the sampling chamber 30.

It is envisioned that the inlet tube 16 may be mass produced by filling the inlet tube with conditioning layer(s) 60 prior to securing the tube to the mounting component 56 and/or prior to final assembly of housing assembly 12. It is understood that the inlet tube 16 may be filled with conditioning layer(s) after the inlet tube is secured to the mounting component 56 and/or after the mounting component is secured to the shell 24.

In one embodiment, the heater 40 of the first detecting segment 32 (e.g., the $O_2$ sensing segment) and the inlet tube 16 are in thermal contact so that heat is transferred from the first heater 40 to the inlet tube and to the conditioner (e.g., the catalyst(s)) in the inlet tube. It should be understood that the inlet tube 16 may not be in thermal contact with a heater on the sensor element without departing from the scope of the present invention. Referring to FIGS. 6 and 7, in the illustrated embodiment, the inlet tube 16 has a generally rectangular cross section and a generally planar contact surface or side of the inlet tube 16 physically contacting the first detecting segment 32 of the sensor element 14. This construction and arrangement provides substantially optimal thermal contact and heat transfer between the heater 40 and the inlet tube 16. It is understood that the inlet tube 16 does not have to physically contact the sensor element 14 to be in thermal contact. The inlet tube 16 may have other cross-sectional shapes within the scope of the invention. For example, the inlet tube 16 may have a generally circular cross section, or a generally D-shaped cross section with a planar side in thermal contact with the heater.

In one example, the conditioner may include a conditioning layer 60 (e.g. a catalyst) that operates optimally at an operating temperature that is the same as or within the same range as the optimal operating temperature of the first sensing component 36. Accordingly, in this example the heater 40 of the first detecting segment 32 provides heat for both the first sensing component 36 segment and the conditioning layer(s) in the inlet tube 16. For example, optimal operating temperature ranges for one type of oxidation catalyst in the inlet tube 16 and for one type of $O_2$ sensing component 32 may be in a range from about 500° C. to about 900° C. and more particularly, between in a range from about 650° C. to about 750° C.

Referring to FIG. 6, the housing assembly 12 includes an inlet port 68 and an outlet port 70 in fluid communication with the respective inlet and outlet tubes 16, 18. The inlet and outlet ports 68, 70 extend generally transversely to the shell 24. In the illustrated embodiment, the inlet and outlet ports 68, 70 are defined by respective inlet and outlet recesses 72, 74 (FIG. 3) formed in the outer face of the mounting component 56 and a cover 76 secured to the outer face of the mounting component. The cover 76 of the illustrated embodiment is constructed as a circular plate or disk of stainless steel and may be secured to the mounting component 56 by welding, such as laser welding, or in other ways. The cover 76 may be of other shapes and may be made of other materials without departing from the scope of the invention. The cover 76 and the mounting component 56 may be formed as a single, unitary structure without departing from the scope of the invention.

Referring to FIGS. 4 and 6, a mounting sleeve 80 and coupling 82 are secured over the shell 24 and are used to secure the housing assembly 12 to the housing mount 20. The mounting sleeve 80 has a cylindrical body and an annular, external flange 84 at a first longitudinal end of the body. As explained in more detail below, for purposes of properly orienting the inlet and outlet tubes 16, 18 with respect to the flow of the gas stream, the mounting sleeve 80 has an alignment key 86 located on the same side or face of the sensor element 14 as the inlet tube and generally aligned with the inlet port 68. Other ways of properly orienting the inlet and outlet tubes 16, 18 with respect to the flow of the gas stream, including other ways of mounting the gas sensor assembly 10 on the exhaust tube 11, do not depart from the scope of the present invention. The mounting sleeve 80 is received over and is secured to the second longitudinal end portion 28 of the shell 24 so that the sleeve is longitudinally spaced from the first longitudinal end portion 26 of the shell. The mounting sleeve 80 may be secured to the shell 24 by welding, such as laser welding, or in other ways. In another embodiment, the mounting sleeve 80 and the shell 24 may be formed as a single, unitary component without departing from the scope of the invention.

The coupling 82 is also received over the second longitudinal end portion 28 of the shell 24. The coupling 82 is positioned between the external flange 84 of the mounting sleeve 80 and the first longitudinal end portion 26 of the shell 24. The coupling 82 includes an annular, externally threaded portion 88 proximate to the external flange 84 of the mounting sleeve 80, and a hexagonal head 90 proximate to the first longitudinal end portion 26 of the shell 24. The coupling 82 rotates freely about the shell 24 and longitudinal movement of a nut along the shell is restricted by the external flange 84 of the mounting sleeve 80 and the larger diameter first longitudinal end portion 26 of the shell.

A housing heat shield 92 secured to the mounting sleeve 80 surrounds the second longitudinal end portion 28 of the shell 24. The housing heat shield 92 is generally cylindrical and has an annular lip 94 abutting the annular external flange 84 or the mounting sleeve 80. The lip 94 or the heat shield 92 may be secured to the flange 84 of the mounting sleeve 80 by welding, such as laser welding, or in other ways. The alignment key 86 on the mounting sleeve 80 is received in a cutout 96 in the housing heat shield 92 so that the key is exposed and projects radially beyond the shield. It is contemplated that the mounting sleeve 80 and housing heat shield 92 may be formed as a single, unitary component instead of being formed separately and subsequently secured together. A reduced-diameter end 98 of the housing heat shield 92 is generally proximate to the inlet and outlet ports 68, 70 but does not cover the ports. The reduced-diameter end 98 provides a tight engagement between the shell 24 and the heat shield 92. Air in an annular space 99 between the shell 24 and the heat shield 92 provides insulation for the shell, particularly electrical components (e.g., heaters 40, 42 and sensing components 34, 36) of the gas sensor element 14, in the shell, as explained in more detail below. It is contemplated that the annular space between the heat shield 92 and the shell 24 may be filled within an insulating material, such as a ceramic material, to provide further insulation. The heat shield 92 may be formed from a deep drawn tube of stainless steel, or may be formed in other ways and from other material.

Referring to FIGS. 5 and 6, the housing mount 20 includes a mounting boss 100 and a boss heat shield 102 secured to the boss. The mounting boss 100 includes a generally cylindrical body having open first and second longitudinal ends, and an external annular flange 104 at the first longitudinal end of the body. The external annular flange 104 is used to secure the housing mount 20 to the exhaust tube 11 or other enclosure in which the gas stream is flowing (FIGS. 1 and 6). An internal surface of the boss 100 at the first longitudinal end is threaded for securing it to the threaded portion 88 of the coupling 82. The opening at the second longitudinal end has a reduced diameter to define an internal annular stop 106 abutting the external flange 84 of the mounting sleeve 80 When the housing 12 is secured to the boss 100. The internal annular stop 106 has a longitudinally extending alignment groove 108 that receives the alignment key 86 on the mounting sleeve 80. A generally triangular orientation marker 110 projects generally transversely from below the external annular flange. As explained in more detail below, the orientation marker 110 and the alignment groove 108 are generally aligned along the length of the boss 100 so that the orientation marker indicates the location of the alignment groove and ensures the gas sensor assembly 10 is properly oriented with respect to the stream of gas.

Referring still to FIGS. 5 and 6, the boss heat shield 102 is generally cylindrical and extends past the second longitudinal end of the boss 100. A free open end of the boss heat shield 102 has a reduced diameter less than an outer diameter of the housing heat shield 92 and a plurality of longitudinally extending slots 103. The slots 103 allow for the open end to expand as the housing assembly 12 passes through the open end so that the boss heat shield 102 tightly engages the housing assembly. The boss heat shield 102 has a cutout 112 for receiving the orientation marker 110 on the mounting boss 100 so that the orientation marker projects transversely beyond the boss heat shield 102. The boss heat shield 102 may be welded, such as by laser welding to the mounting boss 100.

To secure the gas sensor assembly 10 in fluid communication with the gas stream to be sampled, an opening 116 is made in the exhaust tube 11 or other enclosure in which the gas stream is flowing. The housing mount 20 is inserted into the opening 116 so the annular flange 104 of the mounting boss 100 contacts an exterior surface of the tube 11. The housing mount 20 is oriented so the orientation marker 110 faces upstream from the flow of gas. A triangular shaped notch 118 for receiving the orientation marker 110 extends from the opening 116. The housing mount 20 may be secured to the enclosure by welding, such as MIG welding, the annular flange to the enclosure.

After the housing mount 20 is secured to the exhaust tube 11, the sensor housing assembly 12 is inserted into mounting boss 100 so that the alignment key 86 on the mounting sleeve 80 slides into the alignment groove 108 in the mounting boss. The alignment key 86 must be inserted into the alignment groove 108 in order for the housing assembly 12 to be properly secured to the housing mount 20. As disclosed above, the alignment key and the inlet tube 16 lie in a common plane transverse to the shell 24 and are located on the same side of the sensor element 14. Moreover, the housing assembly 12 cannot rotate relative to the mount 20 when the key 86 is received in the groove 108. Accordingly, when the key 86 is inserted in the alignment groove 108, the inlet port 68 faces upstream and, more generally, an entrance of the inlet tube 16 is upstream from an exit of the outlet tube 18. Although not wishing to be bound by any theory, it is believed, under such theory as the Venturi effect, that this arrangement encourages gas from the gas stream to enter the inlet tube 16 and exit the outlet tube 18.

With the alignment key 86 aligned with and/or received in the alignment groove 108, the coupling 82 is threaded into the mounting boss 100. Threading the coupling 82 into the mounting boss 100 moves the housing assembly 12 longitudinally in the housing mount 20 until the external annular flange 84 of the mounting sleeve 80 becomes trapped or locked between coupling and the internal annular stop 106 of the boss. When the housing assembly 12 is secured to the housing mount 20, the housing assembly 12 extends through an open free end of the boss heat shield 102 so the inlet and outlet ports 68, 70 are exposed to the gas stream. Air present in annular space 120 between the housing heal shield 92 and the boss heat shield 102 provides insulation for the shell 24, including the electrical components in the shell (e.g., the sensing components 36, 38) and the conditioner in the inlet tube 16 (e.g., oxidation catalysts). It is contemplated that the annular space 120 may be filled with insulating material, other than air, such as a ceramic material, to provide further insulation.

Figure 8:
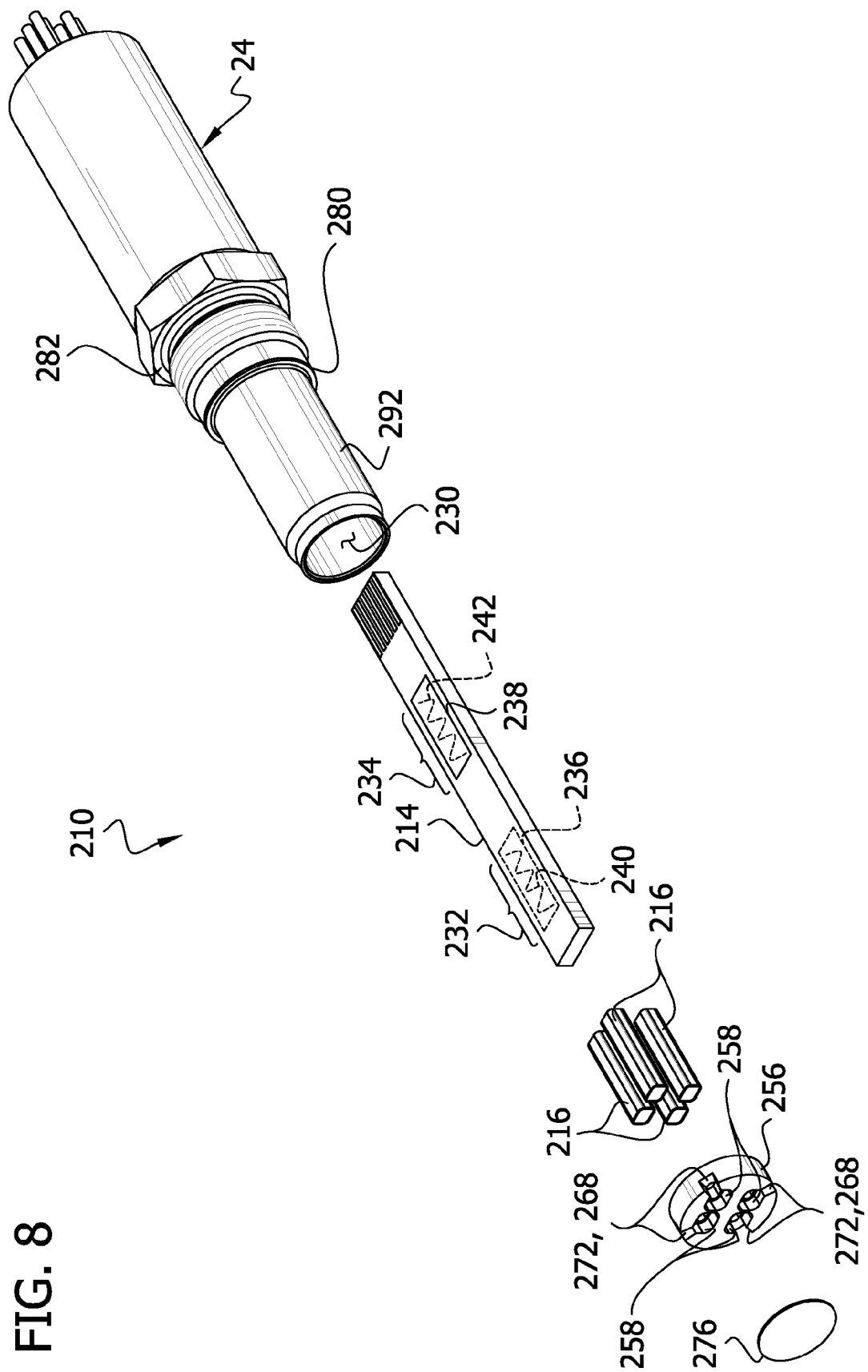
FIG. 8 is a separated perspective of a second embodiment of a housing assembly showing internal components of the assembly.

Referring to FIG. 8, a second embodiment of the housing assembly, hereinafter referred to as "the second housing assembly", is generally indicated at 212. The second housing assembly 212 is substantially identical to the first housing assembly 12, except for the differences noted below. For convenience, similar components are indicated by corresponding reference numerals plus 200. Like the first housing assembly 12, the second housing assembly 212 includes a shell 224, a gas sensor element 214 mounted in the shell, a mounting component 256 secured to an open first longitudinal end of the shell, a cover 276, a housing heat shield 292, a mounting sleeve 280 and a coupling 282. Each of these components may be constructed and assembled in a similar manner as disclosed above with respect to the first housing assembly 12. Moreover, although not illustrated, the second housing assembly 212 may be secured to in exhaust tube 11 using a housing mount including a boss heat shield that is similar to the housing mount 20 illustrated in FIGS. 1, 2, 5 and 6, although as will become apparent, the housing mount for the second housing assembly does not need components for aligning the tubes relative to the flow of the exhaust gas.

One difference between the first housing assembly 12 and the second housing assembly 212 is the present embodiment includes four tubes 216 providing fluid communication between the sampling chamber 230 and outside the housing assembly 212. The four tubes 216 each have a generally rectangular cross section, although the tubes may have other cross-sectional shapes. For reasons explained below, each of the tubes 216 contains desired conditioners (e.g., catalysts) such as the conditioning layers 60 described above with respect to the inlet tube 16 of the first housing assembly 12. Moreover, each of the tubes 216 is in thermal contact with the first heater 240 of the first detecting segment 232. The four tubes 216 are spaced radially on the mounting component 256 so two of the tubes. i.e., a first pair, are on one side or face of the sensor element 214 and the other two tubes, i.e., a second pair, are on the other side or face of the sensor element. In other words, the sensor element 214 is located between the two tubes pairs 216. Four ports 268, each in fluid communication with one of the four tubes 216, are defined by recesses 272 in the mounting component 256 and the cover 276 secured to the mounting component. Each of the ports 268 extends radially with respect to the longitudinal axis L of the shell 224. In the illustrated embodiment the ports 268 are spaced equally circumferential about the entire mounting component 256.

Because the ports 268 of the tubes 216 are equally spaced about the circumference of the mounting component 256 and because each of the tubes includes the desired conditioner, the second housing assembly 212 does not need a specific orientation with respect to the flow of gas. Depending on the orientation of the second housing assembly 212 with respect to the flow of exhaust gas when the housing assembly is secured to the exhaust pipe, ants one or two of the four tubes 216 will function as an inlet tube and one or two of the other tubes will function as an outlet tube. Each of the tubes 216 in the illustrated embodiment has generally planar or flat contact surfaces in thermal contact with the first heater 40 to promote heat transfer. Because the second housing assembly 212 does not need a specific orientation with the flow of exhaust gas, the mounting sleeve 280 does not include an alignment key. Moreover, the mounting boss (not shown) for use with this embodiment does not include an alignment groove or an orientation marker.

Figure 9:
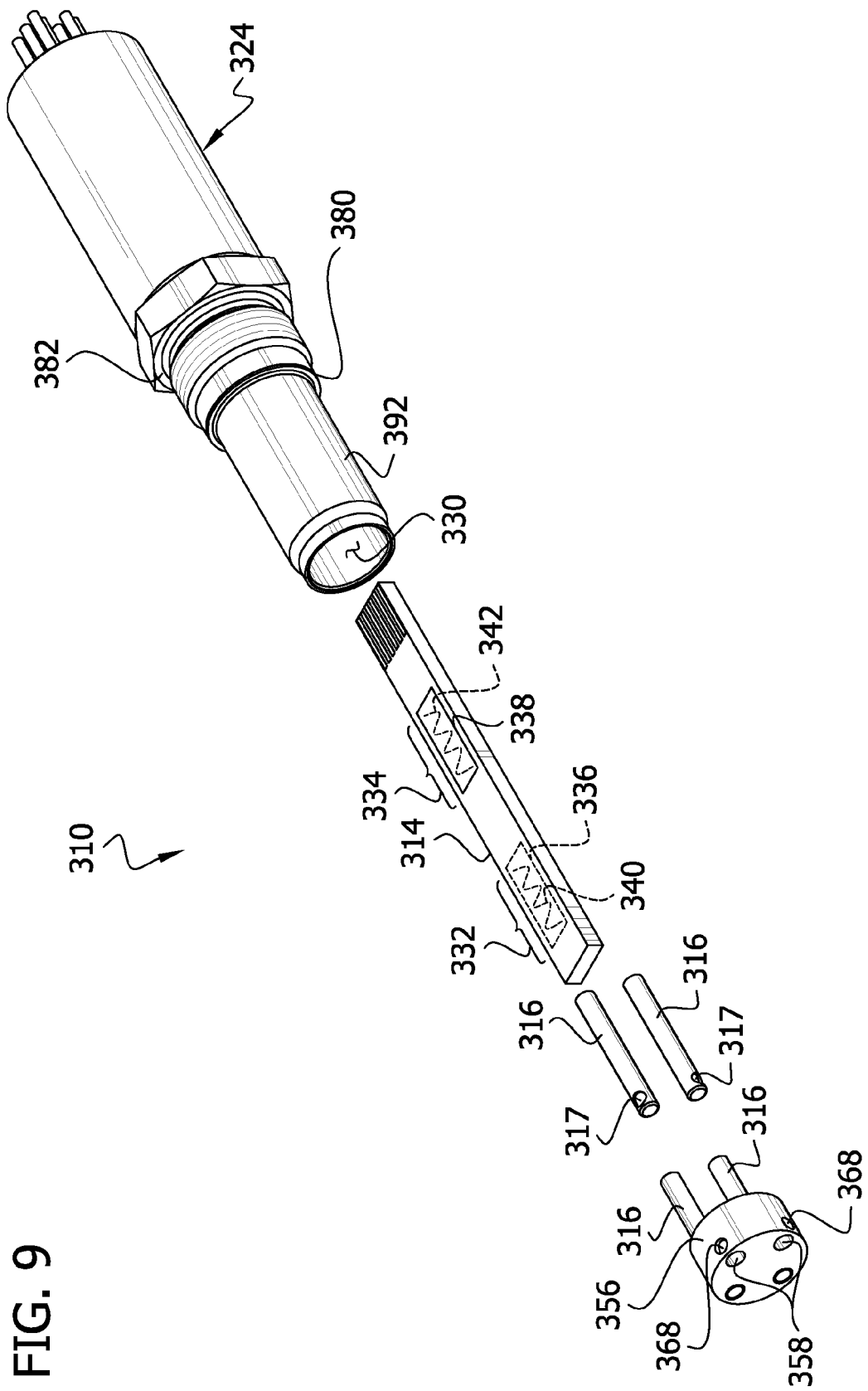
FIG. 9 is a separated perspective of a third embodiment of a housing assembly showing internal components of the assemble.

Referring to FIG. 9, a third embodiment of the housing assembly, hereinafter referred to as "the third housing assembly," is generally indicated at 312. The third housing assembly 312 is substantially similar to the second housing assembly 212, except for the differences noted below. For convenience, similar components are indicated by corresponding reference numerals plus 100. Like the second housing assembly 212, the third housing assembly 312 includes a shell 324, a gas sensor element 314 mounted in the shell, four tubes 316 secured to a mounting component 356, which is secured to an open first longitudinal end of the shell, a housing heat shield 392, a mounting sleeve 380 and a coupling 382. Although each of the tubes 316 has a circular cross section, the tubes are spaced radially on the mounting component 356 similar to the tubes 216 of the second embodiment. The tubes 316 may be in thermal contact with a first heater 340. The tubes 316 may have other shapes without departing from the scope of the invention.

A difference between the second housing assembly 212 and the third housing assembly 312 is that ports 368 for the tubes 316 are defined by openings in the mounting component 356, as opposed to being defined by recesses in the mounting component and a cover, as in the second housing assembly. Each of the ports 368 is in fluid communication with one of the tubes 316 and extends generally transversely or radially with respect to the longitudinal axis L of the shell 324. The ports 368 are equally spaced about an entire circumference of the mounting component 356. Also, unlike the tubes 16, 216 of the first and second housing assemblies 12, 212, respectively, each of the tubes 316 of the third housing assembly 312 have a closed end and a transverse opening 317 adjacent to the closed end, generally transverse to the tube. Each of the transverse openings 317 are generally aligned with one of the ports 368 when the tubes are secured to the mounting component 356 so that the ports are in fluid communication with the tubes. Like the second housing assembly 212, depending on the orientation of the third housing assembly 312 with respect to the flow of exhaust gas when the housing assembly is secured to the exhaust pipe, any one or two of the four tubes 316 will function as an inlet tube and one or two of the other tubes will function as an outlet tube.

Figure 10:
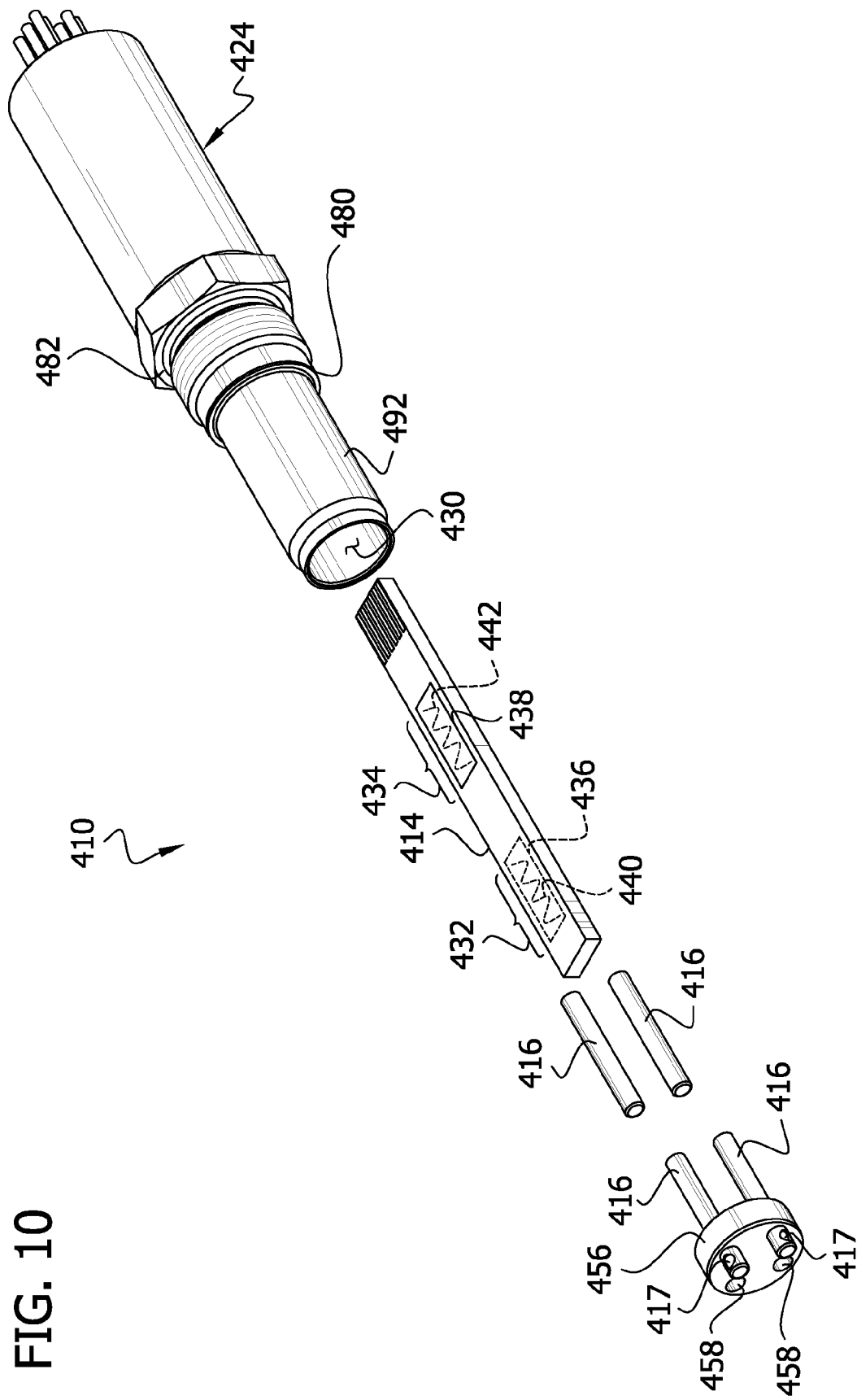
FIG. 10 is a separated perspective of a fourth embodiment of a housing assembly showing internal components of the assembly.

Referring to FIG. 10, a fourth embodiment of the housing assembly, hereinafter referred to as "the fourth housing assembly", is generally indicated at 412. The fourth housing assembly 412 is substantially similar to the third housing assembly 312, except for the differences noted below. For convenience, similar components are indicated by corresponding reference numerals plus 100. Like the third housing assembly 312, the fourth housing assembler 412 includes a shell 424, a sensor element 414 mounted in the shell, a mounting component 456, and four tubes 416 secured to the mounting component, each of which include at least one conditioner (not shown). Each of these similar components may be constructed and assembled in a manner similar to that disclosed above with respect to the third housing assembly 312. The difference between the third housing assembly 312 and the fourth housing assembly 412 is that the mounting component 456 does not include transverse openings in fluid communication With the tubes 416. Instead, longitudinal ends of the tubes 416 of the fourth housing assembly 412 extend through mounting openings 458 in the mounting component 456 so transverse openings 417, extending generally transversely and more specifically, radially, with respect to the longitudinal axis of the shell 424, are exposed.

INDUSTRIAL APPLICABILITY

The present gas sensor assembly 10, 210, 310, 410 can be used in any application where it is desirable to measure a characteristic (e.g., concentration) of one or more constituents in a stream of gas. For example, in one application the gas sensor assembly 10, 210, 310, 410 measures constituent(s) in exhaust gas from an internal combustion engine of the machine 9. In such an application, the gas sensor assembly 10 can be secured to the exhaust tube 11, such as a tailpipe, of an exhaust system of the machine 9 that includes the internal combustion engine. The gas sensor assembly 10, 210, 310, 410 is secured to the exhaust tube 11 so the sampling chamber 30, 230, 330, 430 is in fluid communication with the exhaust stream. With reference to the first sensor assembly 10, during operation of the engine some of the exhaust gas flows into the dedicated inlet tube 16 of the sensor assembly via the transverse inlet port 68. With reference to the second and third sensor assemblies 210, 310, respectively, some of the exhaust gas flows into one or more of the non-dedicated tubes 216, 316 now constituting inlet tube(s), via the corresponding transverse ports 268, 368, respectively that are upstream of the other ports. With reference to the fourth sensor assembly 410, some of the exhaust gas flows into one or more of the non-dedicated tubes 416, now constituting inlet tube(s), via the transverse opening(s) 417 in the corresponding tube(s) that are upstream of the transverse openings in the other tubes.

Regardless of which illustrated embodiment of the gas sensor assembly is employed, the gas is conditioned as it flows through the inlet tube(s) 16, 216, 316, 416. Moreover, in the illustrated embodiments, the inlet tube(s) 16, 216, 316, 416 are in thermal contact with the corresponding first heater 40, 240, 340, 440 of the sensor element 14, 214, 314, 414 so the heater heats the conditioner (e.g., catalyst(s)) to an optimal operating temperature. In addition to the housing heal shield 92, 292, 392, 492, the boss heat shield 102 provides insulation for both the electrical components (e.g., heaters and sensing components) in the shell 24, 224, 324, 424, and for the conditioning layers 60 (e.g., catalysts) in the inlet tubes 16, 216, 316, 416. The insulation provided by the boss heat shield 102 is greater than the insulation provided by the housing heat shield 92, 292, 392, 492 because the annular space 120 between the boss heat shield and the housing heat shield is greater than the annular space between the housing heat shield and the shell 24, 224, 324, 424. This improved insulation provided by the boss heat shield 102 reduces the amount of power needed to drive the first heater 40, 240, 340, 440 and the second heater 42, 242, 342, 442 to maintain the first sensing component 36, 236, 336, 436 (e.g., an $O_2$ sensor), the second sensing component 38, 238, 338, 438, and the conditioning layers 60 (e.g. catalysts) at the respective optimal operating temperatures.

The conditioned gas then flows out of the inlet tube(s) 16, 216, 316, 416 and into the sampling chamber 30, 230, 330, 430 where the gas contacts the first sensing component 36, 236, 336, 436 (e.g., an $O_2$ sensor) and the second sensing component 38, 238, 338, 438 (e.g., a NO$_x$ sensor) of the sensor element 14, 214, 314, 414. The sensing component(s) sends an electrical signal indicative or a characteristic (e.g., concentration) of at least one constituent gas in the sampling chamber 30, 230, 330, 430 to the microcontroller of the machine 9. In one example, the concentration of the constituent gas(es) being measured can be used as a feedback signal so the microcontroller can adjust other operating parameters of the machine.

The conditioned gas then flows into the outlet tube 18, 216, 316, 416, and out of the gas sensor assembly 10, 210, 310, 410, back into the gas stream. Although not wishing to be bound by any theory, it is believed one or more fluid dynamic phenomena, such as the Venturi effect, create low pressure at the transverse outlet port(s) 70 and transverse port(s) and opening(s) constituting outlet port(s) 268, 368, 417 to drive the gas through the outlet tube and back into the gas stream.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than die listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A gas sensor assembly comprising: a housing comprising a first longitudinal end portion and a second longitudinal end portion defining a chamber wherein the second longitudinal end portion has a first end proximate the first longitudinal end portion and an oppositely disposed second end; a gas sensor mounted in the chamber; a mounting component connected to the second end of the second longitudinal end portion and having first and second openings there through placing the exterior of the housing in fluid communication with the chamber; an inlet tube having a first end secured to the first opening of the mounting component and extending into the chamber of the housing, the inlet tube defining a passage providing fluid communication between outside the housing and the chamber of the housing; and an outlet tube having a first end secured to the second opening of the mounting component and extending into the chamber of the housing, the outlet tube defining a passage providing fluid communication between outside the housing and the chamber of the housing, wherein fluid from outside the housing enters the chamber through the first opening and the inlet tube, contacts the gas sensor, and exits the chamber to outside the housing through the outlet tube and the second opening.

2. A gas sensor assembly as set forth in claim 1, wherein the inlet tube contains a catalyst material.

3. A gas sensor assembly as set forth in claim 1, wherein the housing includes a shell having a length extending between opposite longitudinal ends, at least a portion of the gas sensor being between the inlet tube and the outlet tube in a transverse direction relative with respect to the shell.

4. A gas sensor assembly as set forth in claim 3, wherein the gas sensor includes a heating element, the heating element being between the inlet tube and the outlet tube.

5. A gas sensor assembly as set forth in claim 4, wherein a portion of the exterior surface of the inlet tube is in thermal contact with the heating element.

6. A gas sensor assembly as set forth in claim 5, wherein the portion of the exterior surface of the inlet tube in thermal contact with the heating element is generally planar.

7. A gas sensor assembly as set forth in claim 1, further including a cover secured to the mounting component outside the housing, the mounting component and the cover together defining an inlet port at the first opening in fluid communication with the inlet tube and an outlet port at the second opening in fluid communication with the outlet tube.

8. A gas sensor assembly as set forth in claim 3, wherein the inlet port and the outlet port extend generally transversely with respect to the shell.

9. A gas sensor assembly as set forth in claim 1, further including a housing mount, the housing mount including a mounting boss defining an axial opening extending through opposite longitudinal ends of the boss, the axial opening being sized and shaped to receive the gas sensor assembly and to secure the gas sensor assembly to an exhaust system of a machine, and a heat shield extending axially outward from one of the longitudinal ends of the mounting boss with respect to the axial opening of the boss, the heat shield adapted to surround at least a longitudinal portion of the gas sensor assembly when the gas sensor assembly is secured to the boss.

10. A gas sensor assembly as set forth in claim 9, wherein an exhaust system of a machine, to which the gas sensor assembly includes a gas conduit, with the gas conduit defining an exhaust passage through which exhaust gases flow, wherein the housing mount is secured to the gas conduit and extends into the exhaust passage so that at least a portion of the heat shield is in the exhaust passage, wherein the housing is mounted on the housing mount so that the inlet tube is in fluid communication with the exhaust passage.

11. A gas sensor assembly as set forth in claim 1, wherein the mounting component further includes first and second transverse openings fluidly connected to the respective first and second openings and extending generally transversely with respect to the shell.

12. A gas sensor assembly as set forth in claim 3, wherein each of the inlet tube passage and the outlet tube passage includes an exposed transverse opening outside the housing and the mounting component and extending generally transversely with respect to the shell.

13. A gas sensor assembly comprising: a housing defining a chamber and having a length extending between opposite longitudinal ends; a gas sensor in the chamber extending longitudinally with respect to the housing; a mounting component connected to an end of a portion of the housing defining of the chamber and having first and second openings there through placing the interior of the chamber in fluid communication with an exterior of the housing; an inlet tube having a first end secured to the first opening of the mounting component and extending into the chamber of the housing, the inlet tube defining a passage extending longitudinally with respect to the housing and being arranged to provide fluid communication between outside the housing and the chamber of the housing; an outlet tube having a first end secured to the second opening of the mounting component and extending into the chamber of the housing, the outlet tube defining a passage extending longitudinally with respect to the housing and being arranged so as to provide fluid communication between outside the housing and the chamber of the housing; and wherein the gas sensor is positioned between the inlet tube and the outlet tube inside the chamber such that fluid from outside the housing enters the chamber through the first opening and the inlet tube, contacts the gas sensor, and exits the chamber through the outlet tube and the second opening.

14. A gas sensor assembly as set forth in claim 13, wherein the inlet tube includes a catalyst material in the passage of the inlet tube.

* * * * *

UNITED STATES PATENT AND TRADEMARK OFFICE
CERTIFICATE OF CORRECTION

PATENT NO. : 8,057,741 B2  
APPLICATION NO. : 12/341069  
DATED : November 15, 2011  
INVENTOR(S) : Ronald R. Gustin Page 1 of 2

It is certified that error appears in the above-identified patent and that said Letters Patent is hereby corrected as shown below:

In the Specification:

Column 1, line 5, delete "general" and insert -- generally --.

Column 1, lines 46-47, delete "healing" and insert -- heating --.

Column 2, line 22, delete "assembler" and insert -- assembly --.

Column 2, line 29, delete "assembled" and insert -- assembly --.

Column 2, line 38, delete "assemble;" and insert -- assembly; --.

Column 2, line 58, delete "assemble" and insert -- assembly --.

Column 3, line 17, delete "(e.g." and insert -- (e.g., --.

Column 3, line 32, delete "900° C." and insert -- 900° C., --.

Column 3, line 33, delete "Ate" and insert -- The --.

Column 3, line 48, delete "or" and insert -- of --.

Column 4, line 4, delete "16" and insert -- 16, --.

Column 4, line 26, delete "or" and insert -- of --.

Column 4, line 29, delete "gels" and insert -- gas --.

Column 5, line 15, delete "alter" and insert -- after --.

Column 5, line 40, delete "(e.g." and insert -- (e.g., --.

Column 5, line 49, delete "900° C." and insert -- 900° C., --.

Signed and Sealed this  
Twenty-first Day of July, 2015

Michelle K. Lee  
*Director of the United States Patent and Trademark Office*

CERTIFICATE OF CORRECTION (continued)
U.S. Pat. No. 8,057,741 B2

Column 6, line 39, delete "84 or" and insert -- 84 of --.

Column 6, line 40, delete "94 or" and insert -- 94 of --.

Column 6, line 58, delete "within" and insert -- with --.

Column 7, line 8, delete "When" and insert -- when --.

Column 7, line 32, delete "welding" and insert -- welding, --.

Column 8, line 8, delete "heal" and insert -- heat --.

Column 8, line 31, delete "in" and insert -- an --.

Column 8, line 50, delete "tubes." and insert -- tubes, --.

Column 8, line 59, delete "embodiment" and insert -- embodiment, --.

Column 9, line 2, delete "ants" and insert -- any --.

Column 9, line 61, delete "assembler" and insert -- assembly --.

Column 10, line 4, delete "With" and insert -- with --.

Column 10, line 32, delete "respectively" and insert -- respectively, --.

Column 10, line 46, delete "heal" and insert -- heat --.

Column 10, line 62, delete "(e.g." and insert -- (e.g., --.

Column 11, line 3, delete "or" and insert -- of --.

Column 11, line 22, delete "die" and insert -- the --.